(12) United States Patent
Carman et al.

(10) Patent No.: US 6,757,058 B1
(45) Date of Patent: Jun. 29, 2004

(54) FIBER-OPTIC LIGHT LINE FOR USE IN AN INSPECTION SYSTEM

(75) Inventors: George M. Carman, Corvallis, OR (US); Patrick S. Freeman, Brownsville, OR (US)

(73) Assignee: Lucidyne Technologies, Inc., Corvallis, OR (US)

( * ) Notice: Subject to any disclaimer, the term of this patent is extended or adjusted under 35 U.S.C. 154(b) by 0 days.

(21) Appl. No.: 10/031,265

(22) PCT Filed: May 4, 2000

(86) PCT No.: PCT/US00/12335

§ 371 (c)(1),
(2), (4) Date: Oct. 25, 2001

(87) PCT Pub. No.: WO00/66999

PCT Pub. Date: Nov. 9, 2000

Related U.S. Application Data

(60) Provisional application No. 60/132,648, filed on May 5, 1999.

(51) Int. Cl.[7] .............................................. G01N 21/00
(52) U.S. Cl. ...................................................... 356/237.2
(58) Field of Search .......................... 356/237.1, 237.2, 356/237.3, 239.1

(56) References Cited

U.S. PATENT DOCUMENTS

| | | | | |
|---|---|---|---|---|
| 3,559,555 A | * | 2/1971 | Street ........................... | 396/569 |
| 4,101,188 A | | 7/1978 | Yevick ......................... | 350/96.24 |
| 4,738,533 A | * | 4/1988 | Iwamoto ..................... | 356/237.2 |
| 4,827,142 A | | 5/1989 | Hatje ............................ | 250/563 |
| 4,839,635 A | | 6/1989 | Harris et al. ................. | 340/752 |
| 5,247,600 A | | 9/1993 | Williams et al. ............. | 385/115 |
| 5,252,836 A | | 10/1993 | Matthews et al. ........... | 250/571 |
| 5,258,858 A | * | 11/1993 | Chow .......................... | 358/484 |
| 5,401,954 A | * | 3/1995 | Richert ........................ | 250/226 |
| 5,412,220 A | | 5/1995 | Moore ......................... | 250/563 |
| 5,428,365 A | | 6/1995 | Harris et al. ................. | 345/55 |
| 5,448,350 A | | 9/1995 | Kohno ......................... | 356/237 |
| 5,644,392 A | | 7/1997 | Soest et al. ................... | 356/237 |
| 5,684,620 A | * | 11/1997 | Schoon ........................ | 359/298 |
| 5,715,345 A | | 2/1998 | McKinley .................... | 385/115 |
| 5,822,486 A | * | 10/1998 | Svetkoff et al. ............. | 385/116 |
| 5,838,865 A | | 11/1998 | Gulick ......................... | 385/121 |

OTHER PUBLICATIONS

IBM Technical Disclosure Bulletin, NB85036225, vol. 27, #10B, pp. 6225–6226, Mar. 1985.

* cited by examiner

*Primary Examiner*—Michael P. Stafira
(74) *Attorney, Agent, or Firm*—Stoel Rives LLP

(57) ABSTRACT

The present invention employs a blinded fiber-optic light illumination system (12) to illuminate a wood board (24) with a sharp projected light edge to detect the tracheid, color, and geometric characteristics of the lumber during an automated grading process. The light line (70) employs thousands of fibers (46) of desired length (58) and thickness (52). The fibers (46) are randomized such that fibers (46) neighboring each other in the cable (48) do not necessarily neighbor each other in the light line subunit (42) so that the emitted light has substantially uniform intensity over its spatial range. Multiple light line subunits (42) are positioned adjacent to one an other to achieve a desired light line length (60). A set of image sensors (22) in predetermined positions obtain three types of data from the light incident to the board (24). A computer analyzes the data to interpret the physical characteristics of the board (24) and determine how to grade or cut it.

23 Claims, 6 Drawing Sheets

FIBER-OPTIC LIGHT LINE FOR USE IN AN INSPECTION SYSTEM

RELATED APPLICATIONS

This application claims priority benefit of U.S. Provisional Patent Application No. 60/132,648, filed May 5, 1999 and international application PCT/US00/12335, filed May 4, 2000.

TECHNICAL FIELD

The invention relates to an illumination system employed in an inspection process and, in particular, to a blinded fiber-optic light line to illuminate lumber and facilitate the detection of tracheid, color, and geometric characteristics of the lumber during an automated grading process.

BACKGROUND OF THE INVENTION

Until recently, wood processing required human visual inspection. Automation of the inspection process provides more consistent inspection criteria, provides more thorough inspection with faster decision making, permits market-influenced selection of resources, and allows better tracking of the resource pre- and post-processing. To date, however, this type of machine-based optical inspection has been somewhat limited by feature, cost, and safety issues, most of which are derived from difficulties of the available light sources to enhance the optical characteristics of the wood fiber. Moreover, detection and image processing techniques are restricted by the optical characteristics of the image source.

Typically unblinded white light and lasers have dominated attempts to automate the optical inspection process, although other methods have included x-ray and ultraviolet light technologies. Some aspects that are considered when choosing a light source type for lumber inspection include: 1) cost, 2) wood fiber characteristic enhancement ability, and 3) safety.

The initial cost of the light source affects the overall cost of an automated inspection system and thus affects the marketability of the system. Long term replacement costs, including costs of replacement of the light sources and labor-intensive difficulties experienced in performing the replacement, also drive a customer's management decisions for purchase criteria.

Currently, three types of wood fiber detection characteristic enhancements are possible: color spectra response, tracheid effect, and geometric projection. The color spectra response occurs when light (white or specific wavelengths) impinges a board that scatters the incident light. When the scattered light is detected and processed, the reflectance and absorption characteristics of the incident wavelengths by the wood fiber indicate information about the orientation, density, and composition of the wood fiber.

The tracheid effect examines the transmission of incident light through the hollow tracheid tubes that the tree used for transferring water from the root to the leaves. The transmission pattern can provide useful information about the natural fiber structure of the wood by detecting the emitted light at a given distance. This information is particularly useful when an exact location of the origin of the light source is known.

Information about the contour of the surface of wood can be gathered by observing the change in position of a hard-edged light as viewed from a given angle to the source. This geometric projection technique similarly employs a fixed point of origin, as well as a fixed angle of origin for the light source.

Unblinded white light as a light source is inexpensive and has few safety problems. While capable of highlighting color spectra responses, unblinded white light limits the field of information available due to its unspecific glow.

While laser technology becomes less expensive, the intensity needed for generating and inspecting the tracheid effect increases the safety problems inherent to laser use. Lasers are also limited in the color spectra area, but can produce a tracheid effect and allow geometric contouring. Lasers possess their own unique problems in quality of light as well. For instance, when used over a large field of view, many laser line generating techniques yield a Gaussian or other non-uniform response, limiting the amount of area one laser usefully illuminates. Also, lasers tend to provide a speckled image, introducing noise into the detection process, and are sensitive to vibration, a common problem in the industrial environment.

Accordingly, an inexpensive light source that can perform these and other inspection techniques well in an industrial environment and overcome the aforementioned problems would be greatly desirable.

SUMMARY OF THE INVENTION

An object of the present invention is to provide a system and method for illuminating with a line of light a product for optical inspection.

Another object of the invention is to provide such a method and system that facilitate the inspection of the product by enhancing its optical characteristics detectable in at least two and, preferably three, modes.

A further object of the invention is to provide such a method and system for inspecting a wood product.

In a preferred embodiment, the present invention employs a blinded fiber-optic light line to illuminate a wood board with a sharp projected light edge to detect the tracheid, color, and geometric characteristics of lumber during an automated grading process. The light line employs thousands of fibers from a glass-fiber cable that are spread into a light line subunit of desired length and thickness. The fibers are randomized such that fibers neighboring each other in the cable do not necessarily neighbor each other in the light line so that the emitted light has substantially uniform intensity over its spatial range. Multiple light line subunits are positioned adjacent to one other to achieve a desired light line length.

A set of cameras in predetermined positions obtain three types of data from the light incident to the board. A computer analyzes the data to interpret the physical characteristics of the board and determine how to grade or cut the board. Sequentially with respect to the direction of travel of the wood board, in front and at a 45° angle to the board, a fast camera obtains geometric data of the wood board. A color camera, having a row of pixels for each wavelength of interest, is positioned in front of the light line and nearly perpendicularly to the wood board to obtain color data concerning the grain and defect structures illuminated. A black and white camera is positioned behind a blinder connected to the light line and nearly perpendicularly to the wood board to obtain tracheid data.

Additional objects and advantages of this invention will be apparent from the following detailed description of preferred embodiments thereof, which proceeds with reference to the accompanying drawings.

DETAILED DESCRIPTION PREFERRED EMBODIMENT

Figure 1:
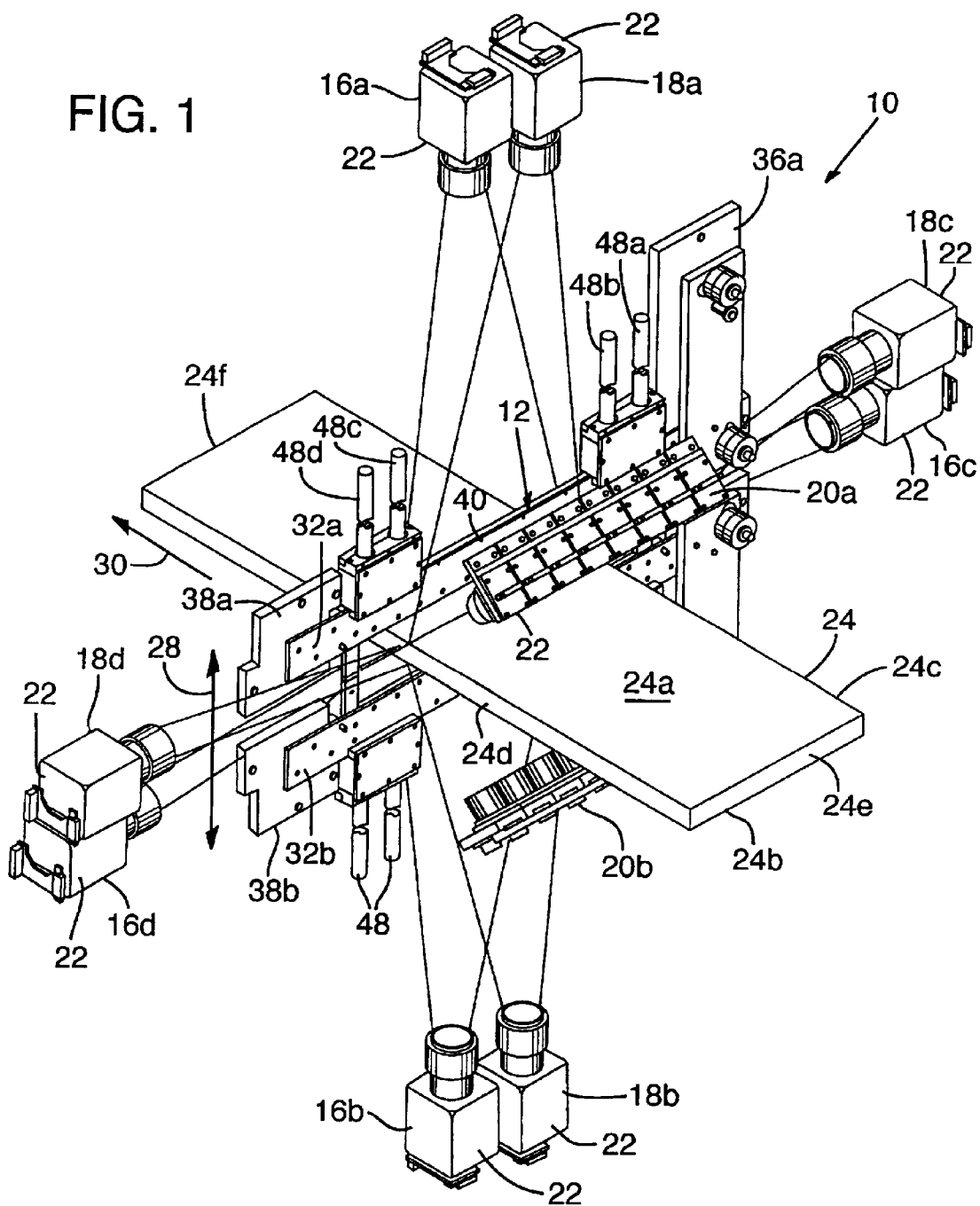
FIG. 1 is a perspective view of an inspection system that includes an illumination system of the present invention.
Figure 2:
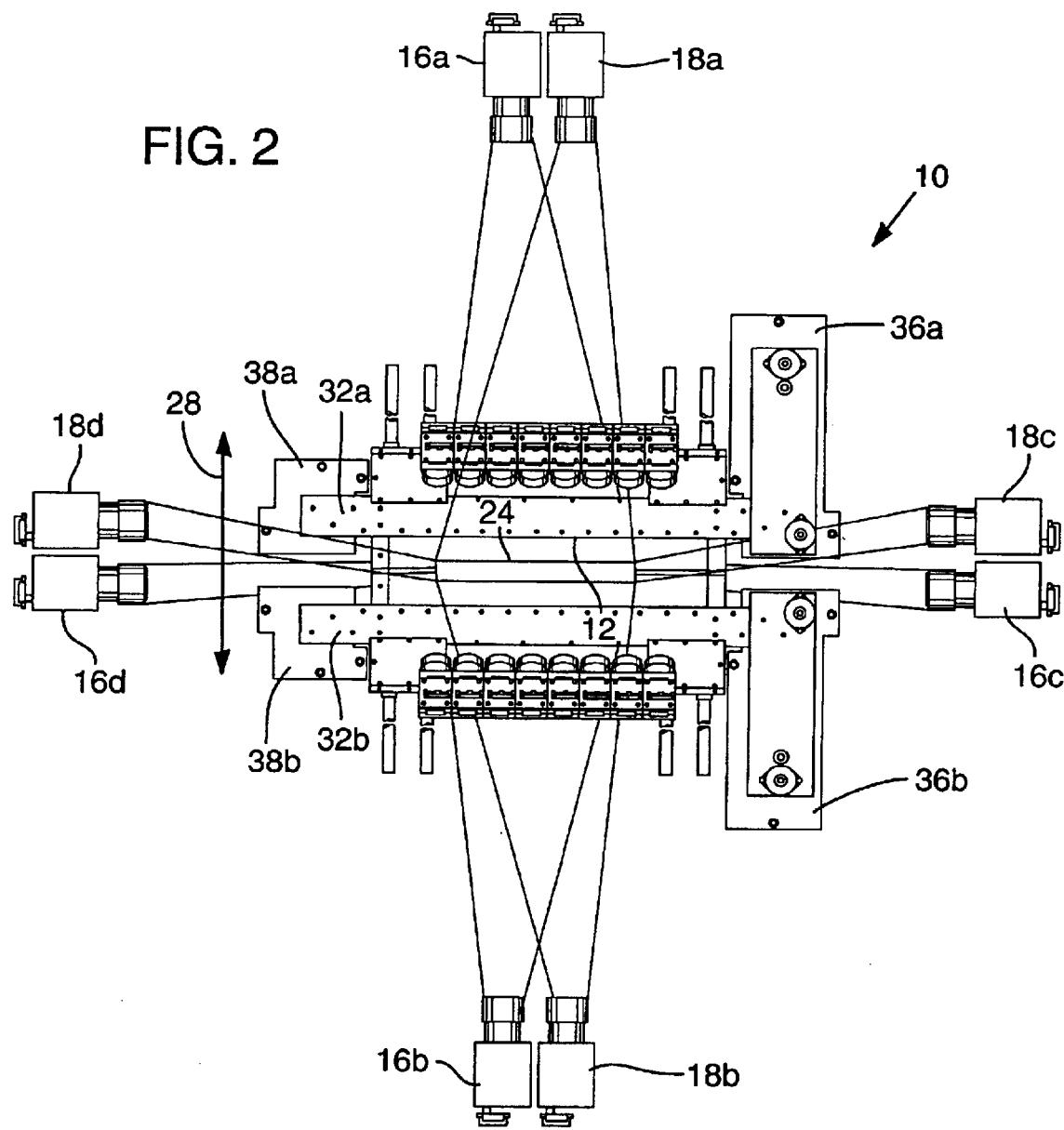
FIG. 2 is a front elevation view of the inspection system of FIG. 1.

FIGS. 1 and 2 show respective perspective and front elevation views of an inspection system 10 that has an illumination system 12 and an image sensing system 14 (FIG. 8) that preferably includes three sets 16, 18, 20 of image sensors 22 for respectively detecting tracheid, color, and geometric characteristics of a wood board 24. With reference to FIGS. 1 and 2, a preferred embodiment of illumination system 12 includes an upper light line housing 26a and a lower light line housing 26b that are generally positioned on opposite sides of a plane 28 that traverses, preferably at perpendicular angles to, a direction of travel 30 of wood board 24.

Figure 3:
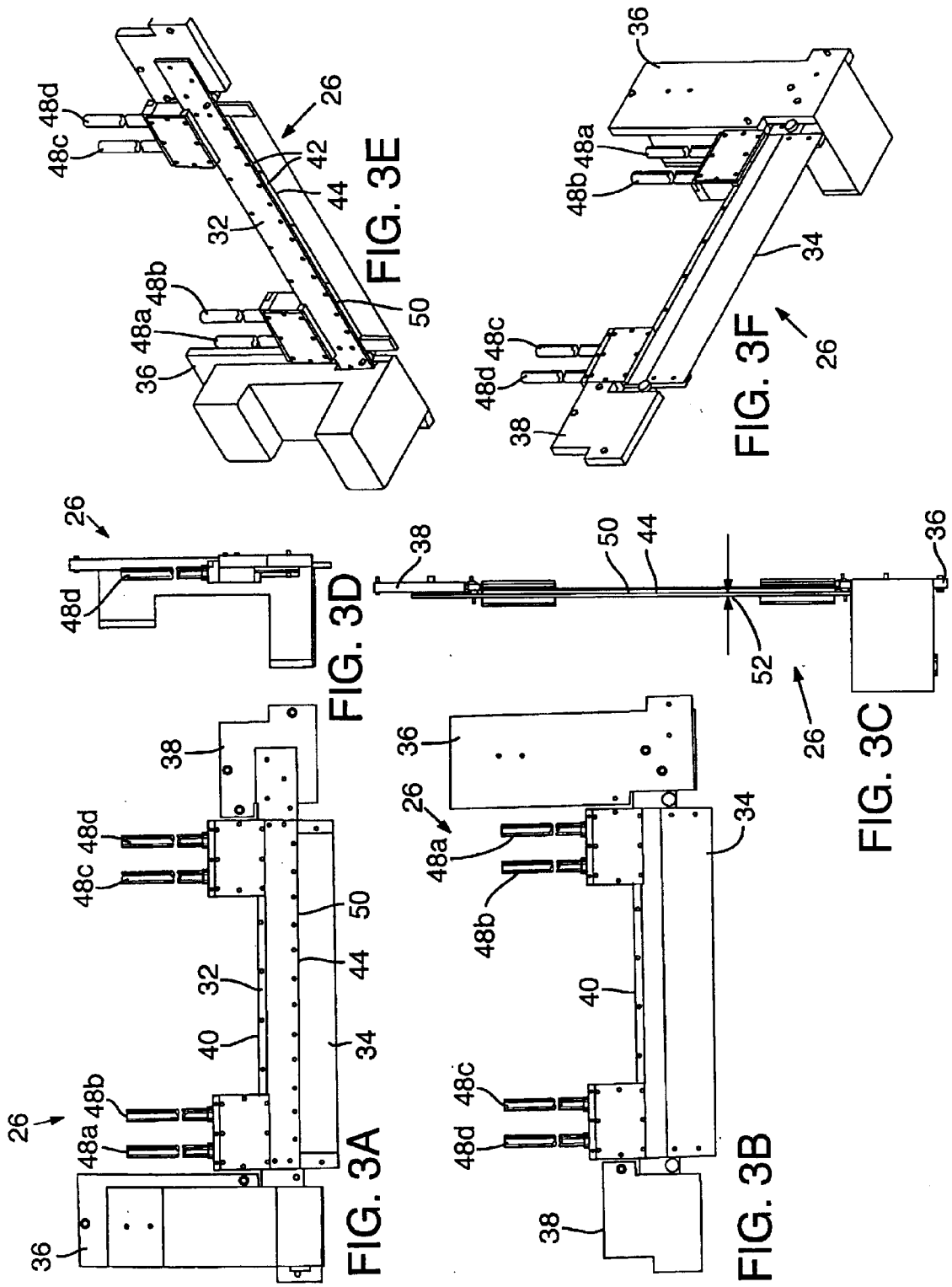
FIGS. 3A, 3B, 3C, 3D, 3E, and 3F are respective front elevation, rear elevation, side elevation, plan, front isometric, and rear isometric views of a light line housing for the illumination system of the present invention.
Figure 4:
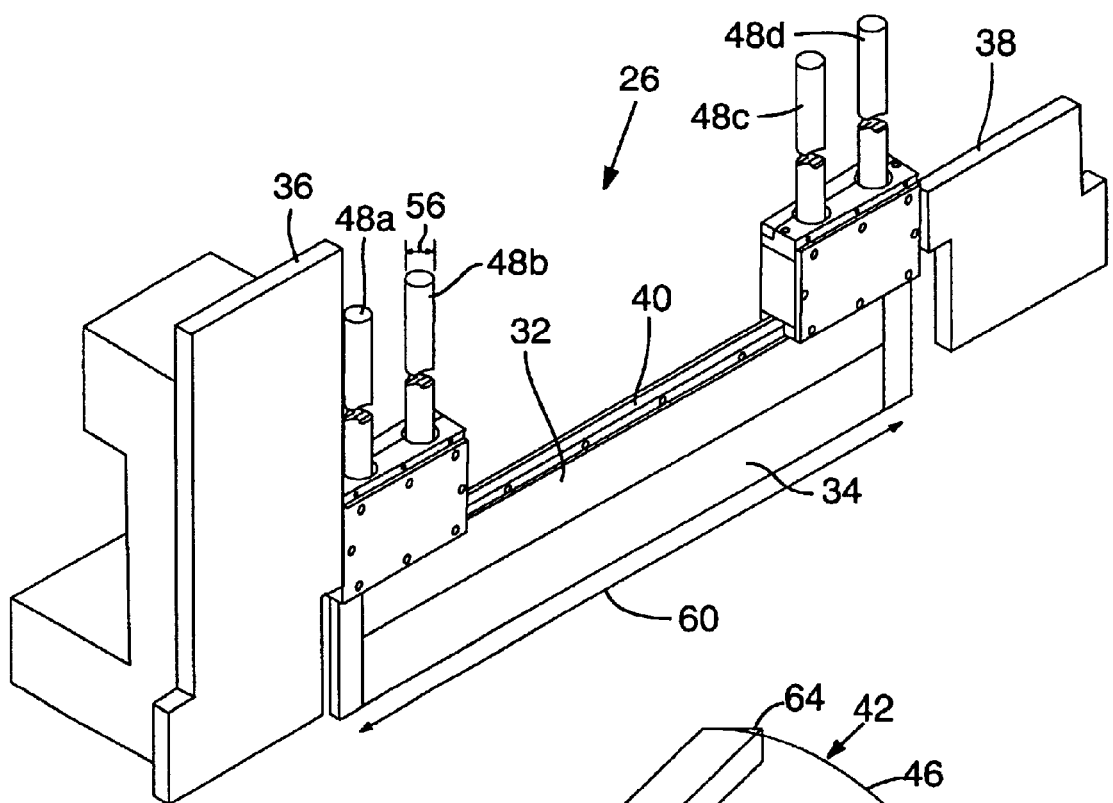
FIG. 4 is a perspective view of the components of the light line housing.

FIGS. 3A, 3B, 3C, 3D, 3E, and 3F (collectively or generically FIG. 3) show respective front elevation, rear elevation, side elevation, plan, front isometric, and rear isometric views of light line housing 26, and FIG. 4 shows an isometric projection view of light line housing 26. With reference to FIGS. 3 and 4, light line housing 26 includes an array alignment plate 32 that may be clamped or otherwise connected to a baffle or light blinder 34. Array alignment plate 32 is held in position and stabilized by a major support unit 36 and a minor support unit 38 that preferably positioned in predetermined locations beyond lengthwise edges 24c and 24d of wood board 24. Skilled persons will appreciate, however, that support units 36 and 38 can alternatively be located beyond widthwise edges 24e and 24f or located at any position along superior surface 40 of light line housing 26. Array alignment plate 32 preferably comprises a reflective or nonreflective metal or rigid plastic or other suitable material that can maintain multiple light line subunits 42 in a linear or planar array.

Figure 5:
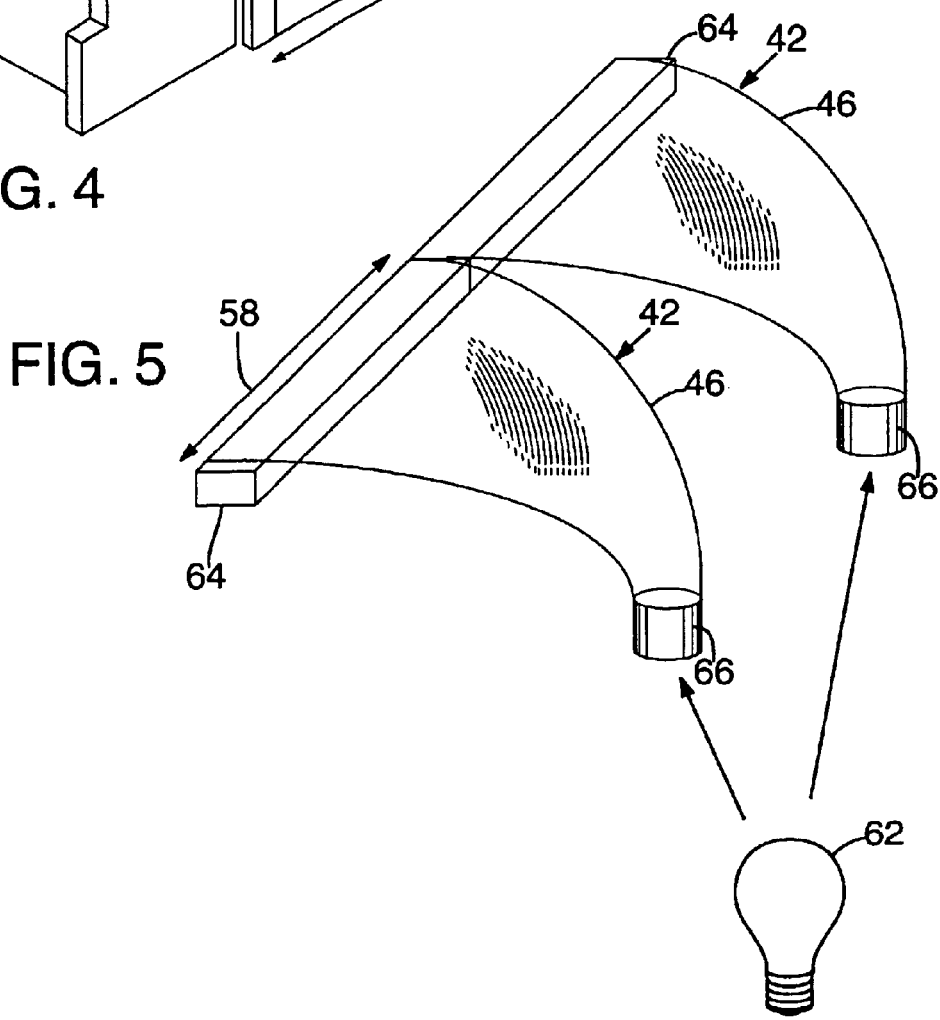
FIG. 5 is an isometric view of two light line subunits used for constructing a light line within the light line housing.
Figure 6A:
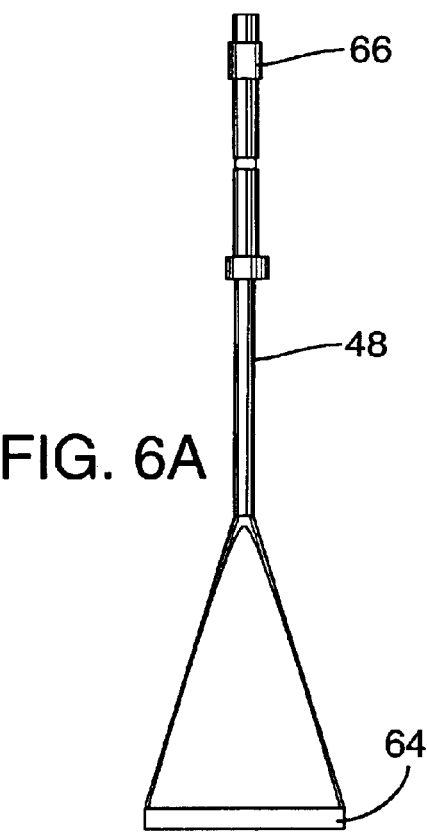
FIGS. 6A, 6B, 6C, and 6D are respective front elevation, rear elevation, first side elevation, and second side elevation views of a light line subunit.
Figure 6B:
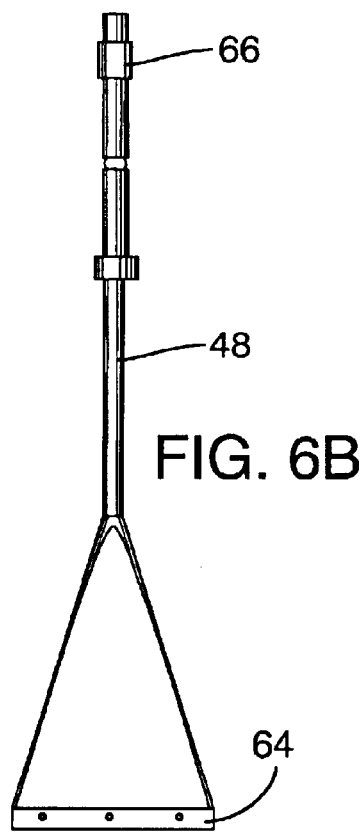
Figure 6C:
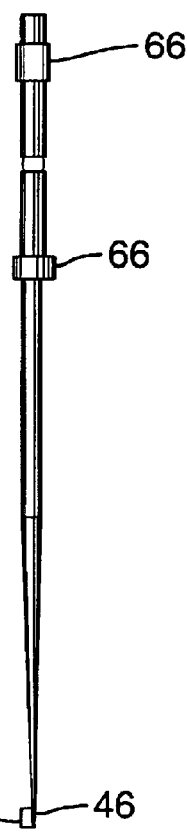
Figure 6D:
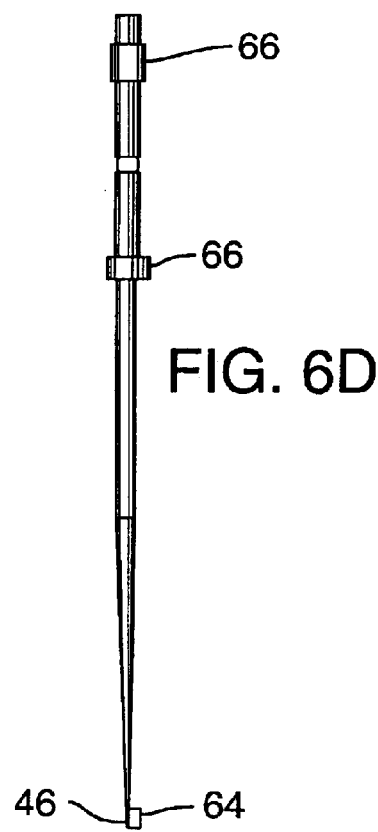

FIG. 5 shows two light line subunits 42 used for constructing a light line source 44 within light line housing 26, and FIGS. 6A, 6B, 6C, and 6D (collectively or generically) are respective front elevation, rear elevation, first side elevation, and second side elevation views of light line subunit 42. With reference to FIGS. 5 and 6, thousands of fibers 46 from an optical-fiber cable 48 are spread into a light line subunit 42 having a slit 50 of desired width 52. Skilled persons will appreciate that infinite variations are possible and that the width 52 of the slit 50 is dependent on the light intensity requirements of image sensing system 14. The width 52 of the slit 50 desired for an inspection application, the diameter 54 of the individual fibers 46, and the diameter 56 of fiber cable 48 can be used to determine the number of rows of fibers 46 and the length 58 of light line subunit 42. Where only a single row of side-by-side fibers 46 is employed in light line subunit 42, the width 52 of the slit 50 is the same as the diameter 54 of fibers 46. Accordingly, a larger cable 48 or a narrower slit 50 yields a longer light line subunit 42. In a preferred embodiment, light line subunit 42 has a slit 50 that is approximately 0.036" (0.9 mm) wide and 5" (127 mm) long. Multiple light line subunits 42 are positioned adjacent to one other to achieve a total light line length 60 desired for a particular inspection application.

The type of fiber 46, including its component glass or polymer, is dependent on the frequency of light suitable for the inspection application. In a preferred embodiment, fibers 46 allow 400—1100 nm transmissions, and their acceptance angle (NA) equals about 0.55 where $\tan^{-1} NA=0.5\angle$, where $\angle$ equals the angle of incidence of light source 62. The diameter 56 of cable 48 can also be adjusted to suit the intensity specifications of a particular inspection application. In a preferred embodiment, a 48" (1.2 m) long, 0.5" (12.7 mm) diameter cable 48 of fibers 46 feeds each light line subunit 42. Fibers 46 are bound together in cable 48 with heat-resistant epoxy, and cable 48 is covered by a Monocoil PVC sheathing.

Figure 7A:
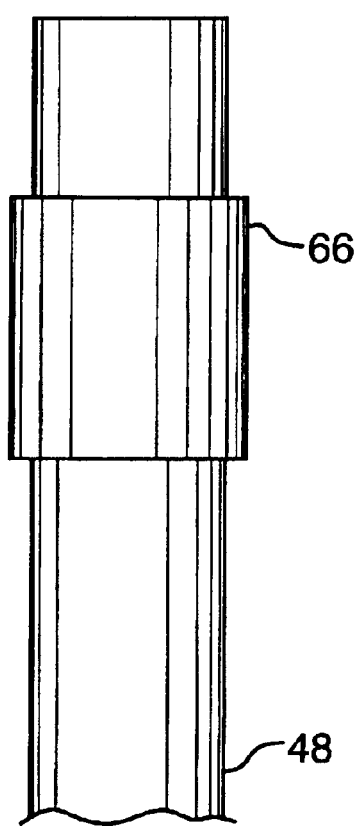
FIGS. 7A and 7B are respective fragmentary frontal and isometric views of a ferrule employed to contain a bundle of fibers.
Figure 7B:
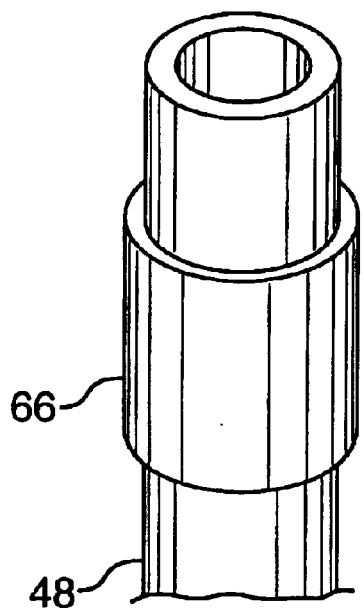

FIGS. 7A and 7B (collectively FIG. 7) are respective fragmentary frontal and isometric views of a ferrule employed to contain a bundle of fibers. With reference to FIGS. 5–7, a similar heat resistant epoxy is employed to bond fibers 46 to one or two substrate strips 64 of light line subunit 42. Preferably, the fibers 46 are spread out from a bundled relationship in cable 48 to be arranged in a contacting side-by-side relationship with each other between the substrate strips 64. Fibers 46 are randomized such that fibers 46 neighboring each other in cable 48 do not necessarily neighbor each other in light line subunit 42 so that light emitted from the slit 50 has substantially uniform intensity over its spatial range. Randomization of fibers 46 to +/−10% variation from their relative positions in cable 48 ensures the homogeneity of the intensity of the emitted light. The emitted light has substantially uniform intensity that varies from less than 20% to even less than 10%. Cable 48 is preferably fed into a ferrule 66 of a type and size determined by the connection available to light source 62 and diameter 56 of cable 48. Cables 48 can be fed through one or more cable support housings 68 that are connected to the superior surface 40 of plate 32.

With reference to FIG. 5, a preferred embodiment of inspection system 10 employs a white light source 62, such as from a 250 W halogen lamp to feed each cable 48. However, skilled persons will appreciate that illumination systems 12 can employ any type or number of light sources 62, particularly high intensity light sources 62 such as one or more lasers, depending on the specific wavelength and intensity requirements of a specific inspection application. The position of light source 62 and any associated optics or reflectors (not shown) can also be adjusted to maximize the angle of acceptance of the type of fiber 46 used. Skilled persons will also appreciate that each subunit 42 can receive illumination from several light sources simultaneously, or multiple subunits 42 can receive illumination from an individual light source 62 or set of light sources.

Figure 8:
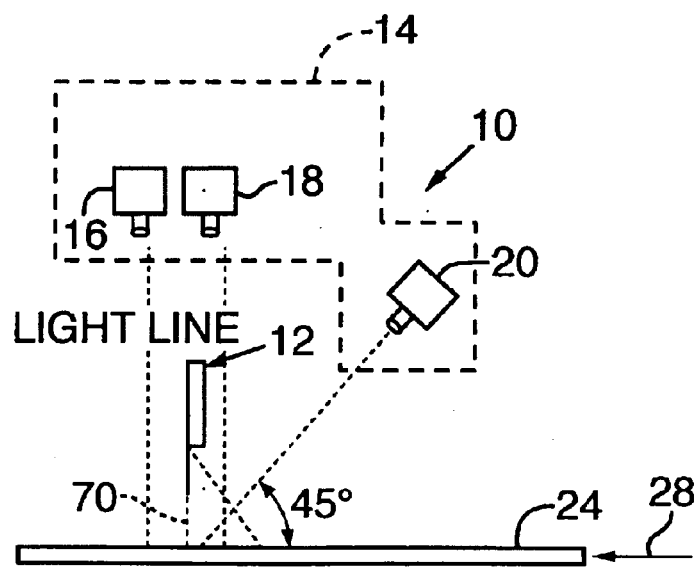
FIG. 8 is a simplified partial side elevation view of the inspection system that shows one set of image sensors of the image sensing system.

FIG. 8 is a simplified side elevation view that shows image sensors 22. With reference to FIGS. 3 and 8, the properties of fibers 46 determine the maximum off axis angle at which light emanates from fibers 46. To facilitate a sharp projected light edge and minimize angular components contained within a light line 70 projected on wood board 24 from slit 50, a light blinder 34 is attached to housing 26. Although light blinder 34 can be positioned to be generally parallel or planar with array alignment plate 32, blinder 34 can be positioned at an optimal angle for the inspection application and in relation to the location of image sensors 22. Such an optimal angle may partly determine or be partly determined by the height of blinder 34 which is preferably short enough to avoid blocking the view of a given image sensor 22 while still able to provide a generally vertical light line 70 having no vignette effect. Due to the line source nature of light line 70, blinder 34 is also preferably sufficiently short enough to avoid decreasing light intensity due to distance. Blinder 34 is also preferably positioned at a distance from wood board 24 to accommodate the optical data acquisition by image sensors 22, and its closeness to wood board 24 is partly limited by its damage susceptibility.

In a preferred embodiment, blinder 34 is removably attached to plate 32 with clamps or other adjustable securing means rather than by bonding to facilitate replacement due to damage or malfunction as well as to facilitate adjustment of its angular orientation with respect to the positions of image sensors 22. Blinder 34 also preferably has sufficient area to supply an ample clamping surface, is rigid enough to preventing wobbling under operating conditions, and is sufficiently sturdy to shield subunits 42 in the event of a bounced wood board 24. The thickness of blinder 34 can be partly determined by its material strength specifications, but can be adjusted so that blinder 34 will avoid obstructing the view from black and white tracheid image sensor 16.

Blinder 34 creates an extremely sharp bright to dark transition that facilitates measurement of the geometric contour and thickness characteristics of wood board 24. Blinder 34 also creates a dark area on wood board 24 that facilitates the acquisition of grain direction and other tracheid information by black and white sensor 16. The bright unblinded area is detected by color sensor 18.

With reference again to FIGS. 1, 2, and 8, image sensing system 14 includes a set of image sensors that are located in predetermined positions to preferably obtain three types of data from the light line 70 incident to wood board 24. Geometric, color, and tracheid data can be obtained substantially simultaneously. Clear wood illuminated by light line 70 tends to transmit light further from the source than defect areas, and gives one part of the visual data. Computers analyze the data to interpret the physical characteristics of board 24 and determine how to grade or cut it.

With respect to the direction of travel 30 of wood board 24, in front and at about a 45° angle to wood board 24, a fast sensor 20 obtains geometric contour data of wood board 24. The field of view of "geometric" fast sensors 20 detects the dark to light transition on wood board 24. The acquired geometric data is then transformed into height coordinate data across wood board 24. With both top and bottom sensors 20a and 20b, the thickness at any location along board 24 can be obtained, and thin or thick cracks or other imperfections can be quantified. Skilled persons will appreciate that the angle does not have to be exact. The angle allows sensor 20 to image the dark to light transition of light line 70 better than if the angle were more extreme. If the angle were closer to 60°, for example, the resolution might suffer.

A color sensor 18, having a row of pixels for each wavelength of interest, is positioned in front of housing 12 and nearly perpendicularly to wood board 24 to obtain, by diffuse reflection, color data concerning the grain and surface defect structures illuminated. Black and white sensor 16 is positioned behind blinder 34 and nearly perpendicularly to wood board 24 to obtain tracheid data. Sensors 16 and 18 are preferably multiple line scan cameras and are best positioned as close to 90° as possible to the planes of the wood surfaces. With respect to sensors 16, for example, the transmittance of light is a function of the image distance to the dark to light transition of light line 70, as well as the characteristics of wood. If not close to 90°, the distance and image will change if the board moves closer or farther from the sensors 16, as can happen if the board is bumped on its way through the scan area.

System 10 can be used in line at a wood processing mill and provides a single pass system that maintains the mill processing speed. The scan data can be displayed on a monitor, fed directly to cutting analysis software, or saved electronically for later cutting optimization.

Calibration is preferably performed with a uniform synthetic material instead of a clear piece of lumber to prevent system 10 from being skewed by natural variations in wood fiber. The uniform calibration permits system 10 to be more sensitive to the characteristics of actual lumber.

With respect to "tracheid" black and white sensors 16 (16a, 16b, 16c, and 16d), a calibration material may, for example, be an opal glass that transmits light. The calibration material is preferably placed so that each light line 70 is illuminating it, and so the sensors 16 are imaging the dark region behind blinder 34. The signal from light source 62 across the field of view of sensors 16 can then be normalized to the intensity of light variation projected across the calibration material and subsequent boards 24. This calibration is also preferably done with respect to color sensors 18 (18a, 18b, 18c, and 18d) as well.

It will be obvious to those having skill in the art that many changes may be made to the details of the above-described embodiment of this invention without departing from the underlying principles thereof. The scope of the present invention should, therefore, be determined only by the following claims.

It is claimed:

1. An illumination system in an inspection system, comprising:
   a light input array including light input ends of closely packed elongate optical fibers, the optical fibers having a cross-sectional dimension, and the input array having an array surface dimension greater than the fiber cross-sectional dimension;
   a substantially linear light output array including adjacent light output ends of the optical fibers;
   a light source for emitting light into the light input array, the optical fibers being adapted for propagating the light and emitting it from the light output array, the light output array being adapted for producing a light line that impinges on an inspection target comprising wood; and
   an image sensing system that includes at least a first image sensor for obtaining optical information about the target in response to the light line impingement on the target.

2. The illumination system of claim 1 further comprising:
   first and second optical fibers having respective first and second input ends that are adjacent in the input array and respective first and second output ends that are collinear and separated by at least a third output end in the light output array.

3. The illumination system of claim 1 in which the image sensing system detects target geometric data.

4. The illumination system of claim 3 in which the image sensing system detects tracheid data.

5. The illumination system of claim 4 in which the image sensing system detects color data.

6. The illumination system of claim 3 in which the image sensing system detects color data.

7. The illumination system of claim 1 further comprising:
a blinder in proximity to the light output array to create a dark area on a surface of the target to facilitate detection of tracheid data by the image sensing system.

8. The illumination system of claim 7 in which the blinder is positioned adjacent to and parallel with the light output array.

9. The illumination system of claim 8 in which the blinder determines a blinder plane that is transverse to the target, the light output array is positioned on a first side of the blinder plane, and the image sensing system comprises a black and white tracheid image sensor positioned to obtain tracheid data from a different second side of the blinder plane.

10. The illumination system of claim 9 in which the image sensing system comprises a color image sensor positioned to obtain target surface data from the first side of the blinder plane.

11. The illumination system of claim 9 in which the image sensing system comprises a fast image sensor positioned to obtain target geometric data from the first side of the blinder plane.

12. The illumination system of claim 11 in which the target determines a target plane and the image sensing system comprises at least one tracheid image sensor and at least one fast image sensor positioned on each side of the target plane.

13. A method for detecting characteristics of lumber having first and second opposing surfaces, comprising:
directing light into input ends of a bundle of closely packed optical fibers;
impinging the first surface of lumber with the light in a form of a light line from a light output array of output ends of the optical fibers;
employing a blinder, positioned in proximity to the light output array and defining a blinder plane transverse to the lumber between first and second blinder sides such that the light output array is positioned on the first blinder side, to create a dark area on the first surface on the second blinder side and create a light area on the first surface on the first blinder side;
obtaining geometric data from the light area; and
substantially simultaneously obtaining tracheid data from the dark area.

14. The method of claim 13 further comprising:
directing light into second input ends of a second bundle of closely packed second optical fibers;
impinging the second surface of lumber with the light in a form of a second light line from a second light output array of second output ends of the second optical fibers;
employing a second blinder, positioned in proximity to the second light output array and substantially coplanar with the blinder plane, to create a second dark area on the second surface on the second blinder side and create a second light area on the second surface on the first blinder side;
obtaining geometric data from the second light area; and
substantially simultaneously obtaining tracheid data from the second dark area.

15. The method of claim 13 further comprising employing an image sensing system that detects color data.

16. The method of claim 14 further comprising employing an image sensing system that detects color data.

17. The method of claim 13 in which the blinder is positioned adjacent to and parallel with the light output array.

18. The method of claim 13 in which the target determines a target plane, further comprising employing an image sensing system that has at least one tracheid image sensor and at least one fast image sensor positioned on each side of the target plane.

19. The method of claim 14 is in which the target determines a target plane, further comprising employing an image sensing system that has at least one tracheid image sensor and at least one fast image sensor positioned on each side of the target plane.

20. An illumination system in an inspection system, comprising:
a light input array including light input ends of closely packed elongate optical fibers, the optical fibers having a cross-sectional dimension, and the input array having an array surface dimension greater than the fiber cross-sectional dimension;
a substantially linear light output array including adjacent light output ends of the optical fibers;
a light source for emitting light into the light input array, the optical fibers being adapted for propagating the light and emitting it from the light output array, the light output array being adapted for producing a light line that impinges on an inspection target;
an image sensing system that includes at least a first image sensor for obtaining optical information about the target in response to the light line impingement on the target; and
a blinder in proximity to the light output array to create a dark area on a surface of the target to facilitate detection of tracheid data by the image sensing system.

21. The illumination system of claim 20 in which the image sensing system detects color data.

22. The illumination system of claim 20 in which the blinder is positioned adjacent to and parallel with the light output array.

23. The illumination system of claim 20 in which the target determines a target plan and the sensing system has at least one tracheid image sensor and at least one fast image sensor positioned on each side of the target plane.

* * * * *

UNITED STATES PATENT AND TRADEMARK OFFICE
CERTIFICATE OF CORRECTION

PATENT NO. : 6,757,058 B1
DATED : June 29, 2004
INVENTOR(S) : George M. Carman and Patrick S. Freeman It is certified that error appears in the above-identified patent and that said Letters Patent is hereby corrected as shown below:

Title page,
Item [57], ABSTRACT,
Line 6, insert -- that are spread into a light line subunit (42) -- after "thousand of fibers (46)";
Line 12, "an other" should read -- another --;
Line 17, insert -- A fast sensor (20) obtains geometric data of the board (24); a color sensor (18) obtains color data concerning the grain and defect structures illuminated; and a black and white sensor (16) obtains tracheid data -- after "incident to the board (24)".

Column 5,
Line 44, "further" should read -- farther --.

Column 8,
Line 21, "claim 14 is in" should read -- claim 14 in --;
Line 55, "plan" should read -- plane --;
Line 55, insert -- image -- before "sensing system".

Signed and Sealed this

Seventh Day of December, 2004

JON W. DUDAS
*Director of the United States Patent and Trademark Office*